United States Patent [19]

Keller

[11] Patent Number: 5,192,356
[45] Date of Patent: Mar. 9, 1993

[54] METHOD AND COMPOSITION FOR TREATING SPLIT-SHELL CROPS

[76] Inventor: Charles H. Keller, 9005 Vista Rd., Chowchilla, Calif. 93610

[21] Appl. No.: 748,266

[22] Filed: Aug. 21, 1991

Related U.S. Application Data

[63] Continuation-in-part of Ser. No. 158,567, Feb. 22, 1988, Pat. No. 5,043,005.

[51] Int. Cl.$^5$ .................. A01N 59/06; A01N 37/02
[52] U.S. Cl. ............................. 504/187; 71/31; 71/58; 71/63; 71/113; 504/190
[58] Field of Search ............ 71/65, 31, 33, 83, 119

[56] References Cited

U.S. PATENT DOCUMENTS 5,043,005  8/1991  Keller et al. ................... 71/65

Primary Examiner—Richard L. Raymond
Assistant Examiner—B. Bembenick
Attorney, Agent, or Firm—Limbach & Limbach

[57] ABSTRACT

Method and composition is disclosed for increasing the percentage of split-shell to non-split crops produced during crop harvest by the pre-harvest application of an aluminum treatment to crop plants.

2 Claims, 4 Drawing Sheets

1. NORMAL LEAF LEVEL
2. MARGINAL LEVEL
3. CORRECT LEAF LEVEL AT THESE DATES.
4. EXCESS LEVEL AT THESE DATES.

METHOD AND COMPOSITION FOR TREATING SPLIT-SHELL CROPS

RELATED APPLICATION DATA

The present application is a continuation-in-part of commonly-owned and co-pending patent application Ser. No. 07/158,567, filed Feb. 22, 1988, now U.S. Pat. No. 5,043,005.

DESCRIPTION

1. Technical Field

The present invention relates generally to the cultivation and harvesting of shelled crops which are usually sold with split shells. More particularly, the invention relates to a new method for treating such crops to increase the percentage of split-shelled crop harvested, and to a composition for such treatment.

2. Background of the Invention

In its broadest sense, agriculture comprises the entire range of technologies associated with the production of useful products from plants and animals. It is the means by which the resources of land, water and sunlight are converted into useful products. The primary agricultural products consist of crop plants for human food and animal feed and livestock products. American agriculture has provided a great diversity of food and fiber crops at lower costs than other nations.

Agricultural crop plants are generally divided into categories, such as grain crops, seed crops, sugar crops, fiber crops, and nut crops, among others. This system of classification relates to the form of the end product; a distinct system can be based upon the commonality of the plant structure which is harvested. The common organs of high plants, such as herbaceous dicotyledonous plants, include three reproductive organs: flower, fruit and seed; and three vegetative organs: root, stem and leaf. From this standpoint, many distinct categories of crop plants, such as fiber crops or nut crops, may be harvested from the same generic organ of distinct plant species. In particular, the generalized "fruit" of the higher plant is the source of the pistachio nut crop and the cotton fiber crop.

The fruits of higher plants have been classified on the basis of numerous criteria, including dehiscence versus indehiscence and dry versus fleshy texture. Dehiscent dry fruits are often called pods and have areas of opening called sutures which split upon maturity to release the seeds and other contents.

As a particular example, the pistachio tree, *Pistacia vera*, is a deciduous tree noted for its edible nuts. Native to arid regions of Asia and Asia Minor, pistachio trees are grown primarily in the Mediterranean region, Italy, Turkey, Iran, Greece and the Soviet Union as a nut crop. Within recent years, the United States has also been producing a substantial pistachio nut crop.

Since the pistachio cannot be propagated from cuttings, seedling rootstocks of *Pistacia atlantica*, *Pistacia terbinthus*, and *Pistacia integerrima* are often grafted with the *Pistacia vera* cultivar, as these stocks are more resistant to soil-borne organisms.

The green or reddish oval fruits, generally three-fourths to one inch in length, are borne in clusters (racemes) on previous years vegetative growth of the pistachio tree. The fruit consists of an outer, fleshy hull (epicarp) containing a thin, tough shell. This hard shell contains the usually light-green nut kernel. The pistachio hull usually splits (dehisces) at maturity and is easily separated from the shell at harvest time.

The shell encasing the pistachio nut is divided by a longitudinal seam (suture) consisting of living cells. This seam also splits prior to nut harvest, in most of the nut crop, resulting in a split-shell nut.

In harvesting pistachio nuts, the tree is shaken mechanically, to remove the nuts. The nuts are hulled immediately and dried.

The hulled nuts are separated from the blanks by an airleg or water bath flotation before drying and then split-shell pistachio nuts are sorted from intact-shell nuts ("non-splits"). The split-shell nuts are then generally roasted and salted, and typically sold as a popular snack food. As split-shells ease shelling by the consumer, these nuts command a higher price. The non-split nuts are cracked mechanically and the nut kernels are sold to the baking, ice cream and confectionery trade.

Although pistachio nuts are grown in California and other parts of the arid Southwest, a substantial commercial industry has been slow to develop in the United States, due in part to the long delay between initial tree planting and nut production, and to the low yields in alternate years.

Native pistachio trees, producing both non-splits and split-shell nuts, may yield more than 20 kilograms of dried in-shell nuts in a good year. However, the trees are noted for their severely alternate bearing habit. In the "off years," non-splits account for 10 to 25% of the crop and the problem substantially worsens in the "on years." This imposes severe financial burdens on pistachio nut growers, since the market value of the non-splits is far below that of the split variety. For example, in 1986 approximately 55 million pounds of split-shell nuts and 20 million pounds of non-splits were produced from 40,000 acres, the non-splits representing over 38% of the average grower's crop (California Pistachio Commission Annual Report 1986/87). These non-split nuts sold for $0.25 per pound before cracking, while the split-shell nuts commanded six times this amount, or approximately $1.60 per pound. The lost income due to non-split nut production amounted to approximately $25 million or over $600 per acre.

As another example of a split-shell crop, the most widely used natural fiber is obtained from cotton plants of the genus Gossypium. A cotton fiber is a single elongated cell contained within the seed pod, commonly called the boll.

Cotton is generally not harvested until the boll dehisces and exposes the fleecy white fiber within. Unfortunately, not all cotton bolls split, nor do they open at the same time, requiring multiple harvests. Therefore, in order to increase the cotton yield and reduce the duplicative effort in a cotton harvest, it would similarly be desirable to increase the percentage and control the timing of the cotton boll splitting.

A resolution to the non-split problem has eluded both growers and university researchers. Experimenters have varied such parameters as fertilization, harvest timing, rootstock, crop variety and cultural practices, all to no avail. It would therefore be desireable to utilize a method to promote shell splitting in shelled crops prior to harvest. It would also be desireable to employ a composition which would promote such shell splitting prior to harvest.

The present invention provides a method, and composition for use therein, which can increase the dehiscence, or splitting, of a crop plant capsule, fruit, pod, etc., without adversely affecting the plant or the use of the crop produce thereby.

BACKGROUND ART

General background information on plant fruits may be found in Fahn, A. and E. Werker, "Anatomical Mechanisms of Seed Dispersal", *Seed Biology*, T. T. Kozlowski, ed., Vol. I (1972) and Schmid, R., "Functional and Ecological Interpretations of Floral and Fruit Anatomy," Bot. Rev. 47 (1981). General background information on cotton plants and crops can be found in Selsom, M. E., *Cotton* (1982).

A general discussion of pistachio nut crops can be found in *Tree Nuts*, AVI Publishing Co., Westport, Conn., pp. 572–603.

A discussion on the role of calcium and calmodulin in plant growth and development can be found in Poovaiah, B. W., Hort. Sci. 20(3):347–352 (1980) and in Berberich, S. et al. "Membrane Research—A Multidisciplinary Treasure Trove," in Agricultural Research, Beltsville Agricultural Research Center, 32(12):8–11 (September 1984).

Publications which disclose the use of organic acids as chelating agents to reduce aluminum toxicity in cells include Suhayda, C. G. and A. Haug, Can. J. Bio. Chem. Cell Biol. 63:1167–1175 (1985) and Physiol. Plant. 68:189–195 (1986).

DISCLOSURE OF THE INVENTION

It has been unexpectedly found that the percentage of split-shelled crops produced per plant can be increased by exposing such plants to an aluminum treatment prior to crop harvest. This new method will enable growers to produce increased quantities of split-shelled crops, thus alleviating the serious financial impact imposed by the large numbers of intact-shell crops currently harvested using conventional methods. Additionally, a novel composition is disclosed for effecting the present method, which may have other useful applications in the agricultural industry.

In accordance with one aspect of the present invention, an aluminum treatment is applied to selected crop plants for times and under conditions sufficient to increase the proportion of split-shelled versus non-split produce, relative to plants not so treated. The aluminum treatment can be applied, e.g., foliarly or systemically to produce the desired results.

Also provided is a novel composition to be utilized in certain aspects of the present invention, as well as for other agricultural purposes. This composition comprises a mixture of an aluminum in a form capable of producing free ion, a wetting agent, in an appropriate solvent, and, optionally, a cuticle softening agent can be included in the composition.

DETAILED DESCRIPTION OF THE INVENTION

Figure 1:
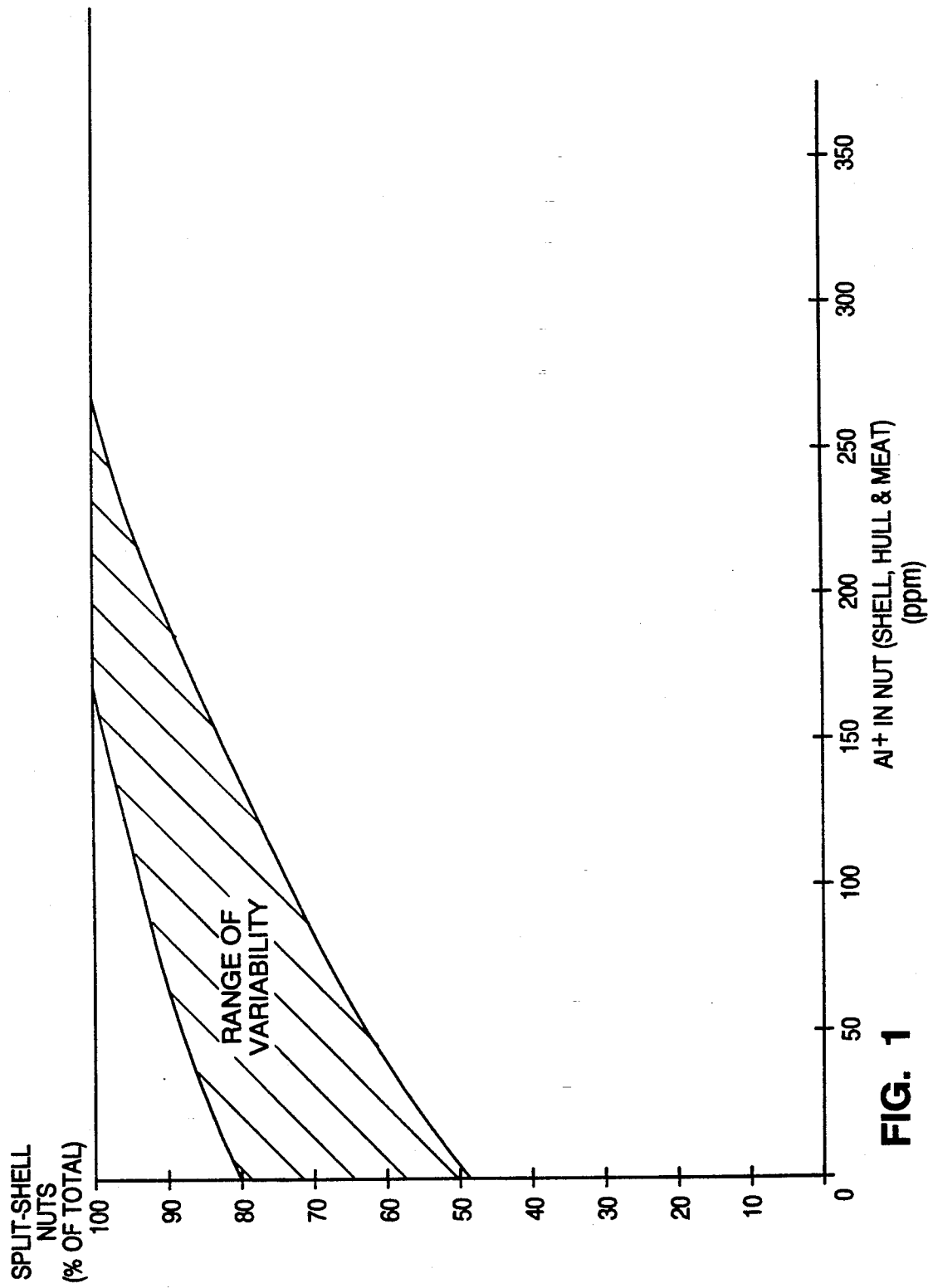
FIG. 1 is a graphic representation relating the percentage of split-shelled nuts as a function of aluminum content after treatments in accordance with the invention applied to pistachio trees.

In accordance with the present invention, a novel method for treating plants producing shelled crops is provided which significantly increases the percentage of split-shelled crops produced by treated plants. The present disclosure also provides a new composition to be used in practicing certain aspects of the present invention.

Although the present invention is described with reference to selected plants producing shelled crops, specifically pistachio trees and cotton plants, it will be recognized that the invention will have application to numerous other plants which produce a crop in a shell. The invention will have particular value when applied to a crop which commands a premium price for split-shelled produce, or where the split-shelled crop significantly decreases the cost of preparing the produce for subsequent sale.

Throughout the present disclosure, the term "shell" is used in a broad sense to indicate a covering or integument of the crop portion of a selected plant. It will be recognized that the term "shell" will thus encompass distinct anatomical features depending on the crop under consideration. In particular, the term shell as used herein encompasses the hard outer covering of both the pistachio nut kernel and the cotton fiber.

Although not intending to be bound by any particular theory, a probable foundation for the present invention is that a non-split shelled crop is probably the normal, viable seed product of a mature, healthy plant. A split-shelled product is an aborted seed, which is discarded by the plant.

For example, it is known that pistachio trees, producing both non-splits and split-shell nuts, are severely alternate bearing. In an "on" year the tree has substantial energy reserves and devotes a great deal of energy to vegetative growth and production of seeds. Therefore, non-split nuts account for a greater proportion of the crop because the tree had substantial energy reserves.

After this great expenditure of energy, the tree experiences an "off" year and its low energy reserves result in an increase in the number of split-shelled nuts. Thus, the normal horticultural practices designed to increase the health and longevity of pistachio trees actually contribute to the increase in non-split nuts and the decreased profitability of the nut crop.

It has been determined that a treatment which selectively weakens the seam of the pistachio nut shell, without substantially harming the tree, will increase the split-shell nut productivity.

In addition, it has also been found that the same treatment weakens the seam of the cotton boll shell, without substantially harming the plant, and increases the productivity of split-shelled bolls.

Although the practice of this invention does not depend on the accuracy of any particular theory, it is probable that the benefits of the invention result from some disruption in the cells making up the seam of the shell. Support for this theory is provided by the recent finding that a calcium modulating protein, known as calmodulin, may bind aluminum (Siegel, N. and A. Haug, Biochem. Biophys. Acta. 744:36–45 (1983)). Calmodulin is an intracellular protein which, upon activation by calcium, binds to protein receptors which function to maintain cell wall integrity. It is also known that calmodulin plays an important role in plant growth and development (Poovaiah, B. W., Hort. Sci. 20(3):347–352 (1980)).

Aluminum, on the other hand, is not considered a required micronutrient for most crops, but rather displays toxic effects in plants (Berberich, S. et al., Agricultural Res. 32(12):8–11 (September 1984)). Aluminum is principally used in agriculture as a component of fertilizer compounds to change the foliage color of plants, or to decrease soil pH and thereby increase plant growth. Particular effects of aluminum on either cotton bolls or pistachio trees or nuts are not known to have been previously reported.

Recent investigators have hypothesized that aluminum interferes with calcium metabolism by binding to and causing a resultant change in calmodulin structure and function (Siegel, et al., supra). This alteration renders calmodulin ineffective, thereby causing changes in cell wall rigidity and demonstrating cytotoxic effects (Berberich, S. et al., supra).

As the seams along the longitudinal axes of the pistachio nut shell and the cotton boll shell consist of living cells, this change in calmodulin structure may cause or accelerate mortality in these cells, and may be responsible for the increased splitting in pistachio nut and cotton boll shells observed during the practice of the present invention. However, it may be that aluminum has a different interaction with calmodulin which causes the increase in shell-splitting, or its site of action may be entirely separate from calmodulin.

Therefore, without regard to the actual causal mechanism, one aspect of the invention provides a method wherein an aluminum treatment is applied to selected plants for times and under conditions sufficient to increase the proportion of split-shelled to non-split crops, relative to plants not so treated.

Plants appropriate for treatment in accordance with the present invention include any crop plants wherein the value of the crop produced is enhanced by a splitting of the shell encapsulating the crop end product. By way of example, the pistachio nut crop is considered a desirable subject for such treatment, without regard to the species or cultivar of the Pistacia tree. Similarly, cotton is also considered to be a crop which would benefit from the present treatment, including Upland cotton (*Gossypium hirsutum*), Egyptian, Tanguis and Sea Island cotton (*Gossypium barbadenseum*), Asiatic cottons (*Gossypium arboreum* and *Gossypium herbaceum*), among other cultivated and wild varieties.

The aluminum treatment is most usually carried out not more than 60 days before the crop is ready for harvest, desirably between 30 and 90 days prior to harvest, said treatment being effected so as to maintain a sufficient level of aluminum in the crop so as to increase the amount of shell-splitting thereby. The timing, duration and conditions of the treatment may be adjusted to accommodate various modes of application, environmental conditions and other factors.

In practicing the invention, an aluminum treatment may be used at rates of from 0.1 to 20 kg of aluminum in a form capable of producing free ion, per acre, so as to provide a dosage of approximately 0.001 to 0.1 kg per tree. It will be understood that the amount of aluminum treatment employed per acre or per plant will depend in part on the mode of application, the concentration of aluminum available to affect the plant, the number of plants per acre and numerous other factors.

The treatment of the present invention can be applied by any means which will increase the concentration of ionic aluminum in the shell of the crop and probably in the cells of the longitudinal seam thereof. However, although a common method of treating plants consists of applying the desired substance to the soil, with subsequent uptake through the root system, this method may be less desirable for the treatment of the present invention.

For example, the pistachio tree is known is have a low rate of uptake through its root system. In addition, it is known that aluminum is toxic to plant root tissue and, being highly polar, it would be slow to translocate from the root system, thereby further delaying its desired benefits and increasing its toxic effects on root cells.

Desirable methods of applying the present aluminum treatment are therefore considered to include foliar application or direct systemic application. Direct systemic application of the aluminum treatment to a selected plant can be performed, for example, by injection or by introducing metallic aluminum directly into the trunk or limbs, e.g., with nails, spikes, glaziers points, or other members containing aluminum. However, the metallic aluminum method of direct systemic application may not allow precise monitoring of aluminum translocation and the resultant toxic effects.

Direct injection can be performed by means well known in the art of horticulture, for example by following protocols used to inject systemic fungicides for the control of vascular wilts. The aluminum treatment to be injected may be mixed in any suitable solvent and injected as desired. Due to the low rate of translocation of aluminum through the pistachio tree, systemic injection should minimize aluminum toxicity effects on root cells.

Such a mixture can include simply an aqueous solution of any source of aluminum ions wherein the aluminum as free ion is in a proportion of from approximately 0.01 to 10.0 percent, more usually 0.05 to 5.0 percent and desirably 0.05 to 2.5 percent by weight of the total solution, pH adjusted to a value less than 7.0, desirably less than 5.0.

However, it is considered more desirable to apply the treatment of the present invention by foliar application. Foliar application of the present aluminum treatment affords several advantages over root uptake. For example, as the pistachio tree has a low rate of uptake through the root system, foliar application allows a more direct route to the nut cluster. Additionally, higher levels of aluminum will likely be found tolerable by the plant or tree, since aluminum is highly polar and will resist translocation out of the leaves and rachis to the root, where accumulation and subsequent tree damage might occur.

In accordance with another aspect of the present invention, a composition comprising aluminum in a form capable of producing free ion, a wetting agent and, optionally, a cuticle softening agent, is applied to the plants prior to crop harvest. Desirably, the treatment will be applied foliarly, to obtain the beneficial results while minimizing the risk of harm to the plant.

Desirably, substances which may be used in the aluminum treatment of the present invention will not affect the palatability or subsequent edibility of edible crops which are destined to be harvested. The aluminum treatment of the invention will contain at least one form of aluminum which is capable of exhibiting cytotoxic effects. Typically, this will include free $Al^+$ ions or any aluminum-containing compound that ionizes in solution to produce $Al^+$ ions including, e.g., aluminum sulfate ($Al_2(SO_4)_3$). Of particular value, aluminum-containing compounds employed in the present method are preferably aluminum sulfate or alum (a soluble aluminum sulfate and potassium salt ($AlK(SO_4)_2$)). Such aluminum-containing compounds are often found in fertilizers containing an aluminum component. A particularly desirable form of aluminum sulfate is 96% $Al_2(SO_4)_3$ (food grade, available from Allied Chemical Co.) as used in pickling cucumbers and other foods.

The following aluminum-containing compounds are presently considered to be suitable for the practice of the present invention, without attempting to provide an exhaustive list thereof:

TABLE I

| | |
|---|---|
| $Al_2(SO_4)_3$ | Aluminum sulfate |
| $AlK(SO_4)_2$ | Alum (Aluminum potassium sulfate) |
| CH3CO2Al(OH2) | Aluminum Acetate |
| $AlNH_4(SO_4)_2$ | Aluminum ammonium sulfate |
| $AlNa(SO_4)_2$ | Aluminum sodium sulfate |
| $AlCl_3$ | Aluminum chloride |
| $Al(OH_3)$ | Aluminum hydroxide |
| $Al(NO_3)_3$ | Aluminum nitrate |

In addition, aluminum and aluminum-containing compounds are often contained in other agricultural chemicals, including fungicides. For example, Aliette ®, Mikal ®, and Phodax ® (proprietary compounds composed of aluminum tris-O-phosphonate from Rhone-Poulenc, France) can be employed as aluminum-containing compounds in the practice of the present invention. Thus it will be recognized that many forms of aluminum can be employed in the practice of the invention, so long as the demonstrate the requisite increase in shell splitting.

It is also considered useful to include, in certain treatments particularly adapted for foliar application, a surfactant or wetting agent. The wetting agent functions to alter the surface properties of the pistachio tree leaves, in order to facilitate absorption of the aluminum treatment of the invention. In the practice of the invention, a wetting agent will also desirably not exhibit adverse effects on the foliage, nor interfere with the remaining active components of the aluminum treatment.

Suitable wetting agents include, but are not limited to, non-ionic detergents such as Triton X ® (proprietary compounds from Rohm & Haas composed of octoxynol); polysorbate compounds such as the Tween ® compositions (ICI Americas), Induce ® (a hydrocarbon-based fatty acid diluted with an alcohol available from Helena Chemical), or Nonidet ® (ethylene oxide condensates from Shell Chemical Co.), among others.

It has been found desirable, and the presently preferred agent in certain applications, to employ commercially available detergents, such as Palmolive ® liquid detergent (a proprietary product of the Colgate-Palmolive Co.) as wetting agents in compositions for foliar application. It will be understood that numerous additional wetting agents may be employed, either separately or in combination, in the practice of the present invention.

A selected wetting agent can be included, if desired, at a concentration of from approximately 0.001 to 1.0 percent of the solution, more usually from approximately 0.005 to 0.5 percent. Alternatively, it would be possible to pre-treat the foliage of the selected plant with a wetting agent, or to so treat the foliage after the present aluminum treatment, and retain the benefits of this component of the present invention.

An additional desirable component of an aluminum treatment composition for foliar application can include a cuticle softening agent, such as urea, to soften the waxy, water-resistant coating of the plant leaf. Such an agent would further facilitate absorption of the aluminum treatment into the leaf, so that transport through the conductive tissues into the crop can occur more readily.

In formulating an aluminum treatment of the invention for systemic or foliar application, the various components will ordinarily be dissolved in at least one solvent which does not substantially adversely affect the aluminum, the wetting agent, the selected plant or the crop produced therefrom. Many such solvents exist, and water is considered desirable due to its ready availability and low cost.

It may also be desireable to adjust the pH of the aluminum treatment, as the aluminum is more mobile at acidic pH values.

The amount of aluminum treatment required to obtain the desired effect will be found to vary according to conditions affecting uptake. For example, desirable results can be achieved with an aluminum treatment composed of 96% aluminum sulfate at 10 to 50 pounds per 150 gallons of water per acre of trees, assuming between 135 and 150 pistachio trees per acre. It is to be understood that these figures represent reasonable approximations. However, the upper and lower limits of these parameters will vary depending on many factors including soil pH, the mode of application, the skill and care exercised by the operator, avoidance of waste, and climatic factors such as temperature, the amount of rainfall subsequent to foliar application, among others.

After an aluminum treatment is applied by any of the foregoing methods and crop harvest has terminated, it may be desirable to reduce the amount of residual aluminum in the plant, in order to avoid growth retardation or flower-bud mortality which might affect subsequent harvests. As one means of alleviating such damage, an aluminum chelating compound may be applied to the treated plant in order to bind and remove excess free aluminum ion. Exemplary of such chelating compounds are organic acids, which provide effective ligands for aluminum complexation (Suhayda, C. G. and A. Haug, Physiol. Plant. 68:189-195 (1986); Suhayda, C. G. and A. Haug, Can. J. Biochem. Cell Biol. 63:1167-1175 (1985)). These acids are generally dicarboxylic acids wherein the carboxyl groups are separated by a chain of five or less carbon atoms, e.g.

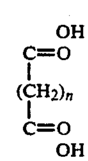

where n=0, 1, 2, 3, 4 or 5.

Alternatively, the carbon chain in an organic acid can include CHOH groups replacing one or more $CH_2$ groups. Representative organic acids include oxalic, malonic, citric, succinic, glutaric, maleic, pimelic and tartaric acids, among others. In particular, a citrate addition (e.g., as $K_2$-citrate) is considered a desirable chelating agent for the complexation and removal of excess free aluminum ion.

Alternatively, a calcium ion source can be applied to the plants, preferably, but not necessarily, by foliar application. The calcium source can be calcium nitrate or any other calcium compound capable of restoring the aluminum - calcium balance, and reversing cytotoxic aluminum effects.

However, it appears that aluminum sulfate ions may be non-phytotoxic (Kinraide, T. B. and D. R. Parker, Physiol. Plant. 71:207–212 (1987)). Therefore, aluminum sulfate appears to be the most desirable source of aluminum ion capable of being used in the aluminum treatment of the invention.

The practice of the present invention can be illustrated by the following examples without, however, implying any limitation to the scope thereof other than in the appended claims.

EXPERIMENTAL

In the examples which follow, all percentages are expressed by weight, and all weights are expressed in pounds, unless otherwise indicated.

In the pistachio crop examples, the trials were conducted on 8, 12 and 14 year old trees of *Pistacia vera* var. Kerman on *Pistacia atlanticus* rootstock, unless otherwise indicated.

EXAMPLE 1

This example describes foliar application of the aluminum treatment of the present invention to pistachio trees in an "off year". Under these circumstances, the proportion of split-shelled nuts in normal (untreated) trees is often as high as 90+ percent. Therefore, the absolute effect of the treatment of the present invention will not be as dramatic due to the high control values.

Samples of aluminum treatment prepared in accordance with the invention contained the following formulations:

TABLE II

| Ingredients | Sample No. 1 | Sample No. 2 |
|---|---|---|
| | (weight in kilograms) | |
| Aluminum sulfate (96%) | 7.25 | 14.0 |
| Palmolive ® detergent | 0.5 | 0.5 |
| Water | 572 | 572 |

The samples were prepared by stirring 16 and 31 pounds of 96% aluminum sulfate, respectively, and 16 ounces of Palmolive ® detergent in 150 gallons of water at room temperature until all solids were completely dissolved. The pH of the final solution was less than 3.0. The addition of aluminum sulfate according to each formulation above produced an aluminum treatment with approximately 1,500 ppm $Al^+$ in sample No. 1 and 3,000 ppm $Al^+$ in sample No. 2. A control sample containing Palmolive ® detergent and water was also employed.

Each sample was applied directly to the foliage of an individual tree by spraying from a hand sprayer. The application continued until the foliage was saturated, generally until fluid run-off from the leaf was observed.

In order to increase the concentration of aluminum in the nut, without excess toxic reaction, different concentrations were applied for different times, thereby maintaining high $Al^+$ concentrations for a sufficient period of time before nut harvest. The results, presented as the percentage of split-shell nuts for each treatment were as presented in Table III.

TABLE III

| Sample | % Split-Shells | % Non-Splits | % Decrease |
|---|---|---|---|
| 1 | 96% | 4% | 50% |
| 2 | 98% | 2% | 75% |
| Control | 92% | 8% | |

As can be seen, in an "off year" the proportion of split-shelled nuts was 92%. However, considering only the non-splits, treatments 1 and 2 caused 50% and 75%, respectively, reduction in non-splits.

EXAMPLE 2

In a second trial of foliar application of the aluminum treatment of the present invention, also in an "offyear", samples of aluminum treatment prepared in accordance with the formulations of Example 1, but containing 31 pounds (Sample 3) and 44 pounds (Sample 4) of 96% aluminum sulfate.

The addition of aluminum sulfate according to each formulation above produced an aluminum treatment with approximately 3,000 ppm $Al^+$ in sample No. 3 and 4,500 ppm $Al^+$ in sample No. 4. A control sample containing Palmolive ® and water was also employed.

Each sample was applied directly to the foliage of an individual tree by spraying from a low-volume electrostatic sprayer (Windmill, Modesto, Calif.). The application continued until the foliage was saturated, generally until fluid run-off from the leaf occurred.

The results, expressed as the percentage of split-shell nuts for each treatment, are shown in Table IV.

TABLE IV

| Sample | % Split-Shells | % Non-Splits | % Decrease |
|---|---|---|---|
| 3 | 99.75% | 0.25% | 87.5% |
| 4 | 99.50% | 0.50% | 75.0% |
| Control | 98% | 2.0% | |

As noted in Example 1, in an "off year" the proportion of split-shelled nuts was 98%. However, considering only the non-splits, treatments 3 and 4 caused approximately 87.5% and 75%, respectively, reductions in non-split nuts produced.

It was found that approximately thirty days were required after application of the treatment solution for the $Al^+$ concentration to reach the desired level in the nut. Earlier treatment at lower $Al^+$ concentration and later treatment at higher $Al^+$ concentrations will also produce the desired shell splitting effects.

Excessive application of the present aluminum treatment can cause foliar deterioration and possible loss of next season's flower buds. Thus, it is considered preferable to apply the solutions as close to harvest as possible, keeping in mind that higher than normal $Al^+$ concentrations are required in the nut to promote splitting.

EXAMPLE 3

This example illustrates a systemic application method in accordance with the present invention.

An aluminum treatment was prepared by mixing approximately 9 g of Aliette ® (Rhone-Poulenc, France; wherein the aluminum is present as aluminum tris-o-ethyl phosphonate) with 1L water. The pH of the solution was adjusted to approximately 2.0 with hydrochloric acid.

This solution was injected into the trunk of a pistachio tree during June by using a high-pressure tree injector which uses a 2½ horsepower engine to develop 600–700 psi and force the treatment solution into the tree through a drilled-out lag bolt brazed to a high pressure coupling.

Approximately 10 days after the aluminum treatment, it was observed that all nuts on the primary limb above the injection site were split. It is known that pistachio nut shell splitting does not normally occur in July. Thus the shell splitting response was due to the external stimulus induced by the aluminum treatment.

In every Example above, samples from aluminum treatment field trials always displayed higher Al+ concentrations in split-shelled nuts and higher percentage of split-shell nuts than control trees not subject to the aluminum treatment.

It was determined in one experiment that the total aluminum level in split-shell pistachio nuts was 225% of the aluminum level in non-split nuts. It was also noted that there was a 1300% difference in aluminum levels in the hulls, a 135% difference in the shells and no difference in aluminum levels in the meats. This clearly indicates that the site of action of the aluminum is most likely in the hull and shell of the pistachio nut.

EXAMPLE 4

It was noted that both Examples 1 and 2 above were performed during an "off year" for pistachio nut harvest, when the relative proportion of split-shelled nuts in a normal crop is high. Thus, the improvement obtained through the practice of the present invention during an "on year" was tested, with even more dramatic results, as the split-shell percentage in the control samples was substantially reduced as the effect of the invention was manifest on a larger proportion of overall crop production.

The treatment of the present invention was applied to various test plots of up to 8.2 acres, using generally the procedure of Examples 1 and 2, except that the solution applied to plot AH used INDUCE ® as a wetting agent and the solution applied to plot AK used 50/50 INDUCE ®/Colgate Palmolive ® as a wetting agent. The results obtained during these "on year" tests were as presented in Table V.

TABLE V

| Test Plot | Days Pre-Harvest | oz/Tree | % Split | % Non-Split | % N-S Nuts |
|---|---|---|---|---|---|
| PW | 33 | 9 | 82.0 | 18.0 | 33.3 |
| Control | | | 73.0 | 27.0 | |
| PE | 13 | 11 | 80.3 | 19.7 | 17.9 |
| Control | | | 76.0 | 24.0 | |
| AH | 40 | >12 | 78.9 | 21.1 | 22.4 |
| Control | | | 72.8 | 27.2 | |
| AK | 35 | >12 | 94.1 | 5.9 | 36.6 |
| Control | | | 90.7 | 9.3 | |
| VI | 62 | >15 | 95.7 | 4.3 | 70.5 |
| Control | | | 85.4 | 14.6 | |
| MP | 76(60) | >15 | 95.5 | 4.5 | 65.9 |
| Control | | | 86.8 | 13.2 | |

The data from the above examples show that the treatment of the present invention applied to pistachio nut trees can provide substantial decrease in the proportion of non-splits produced by the tree, ranging from approximately 18% to 88% reduction in non-splits. As can be seen in FIG. 1, the percentage of non-splits decreases in proportion to the Al+ content measured in the nut.

Figure 2:
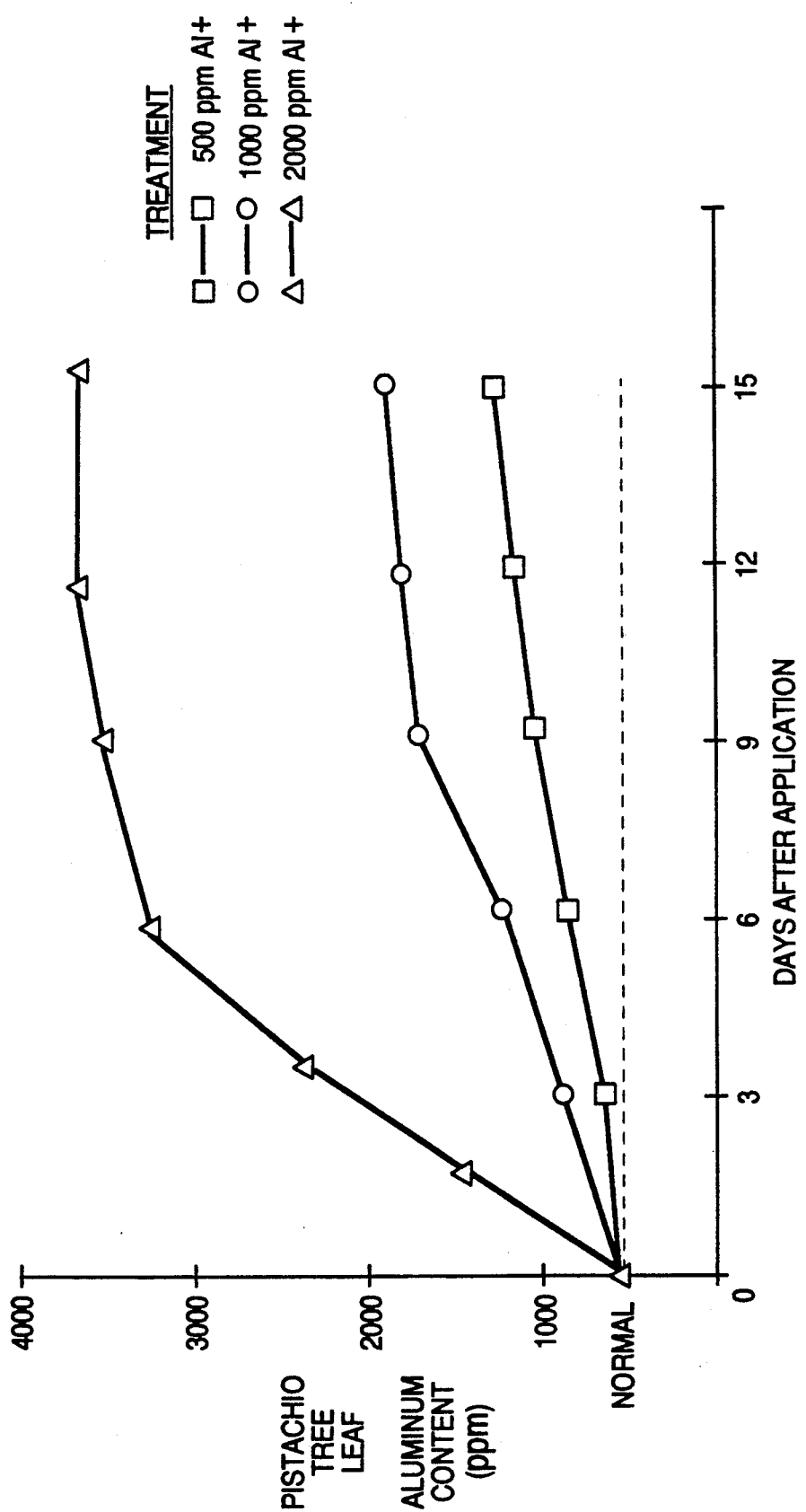
FIG. 2 is a graphic representation relating the aluminum content in the tree leaf to the time since the application date of aluminum treatments in accordance with the invention applied to pistachio trees.
Figure 3:
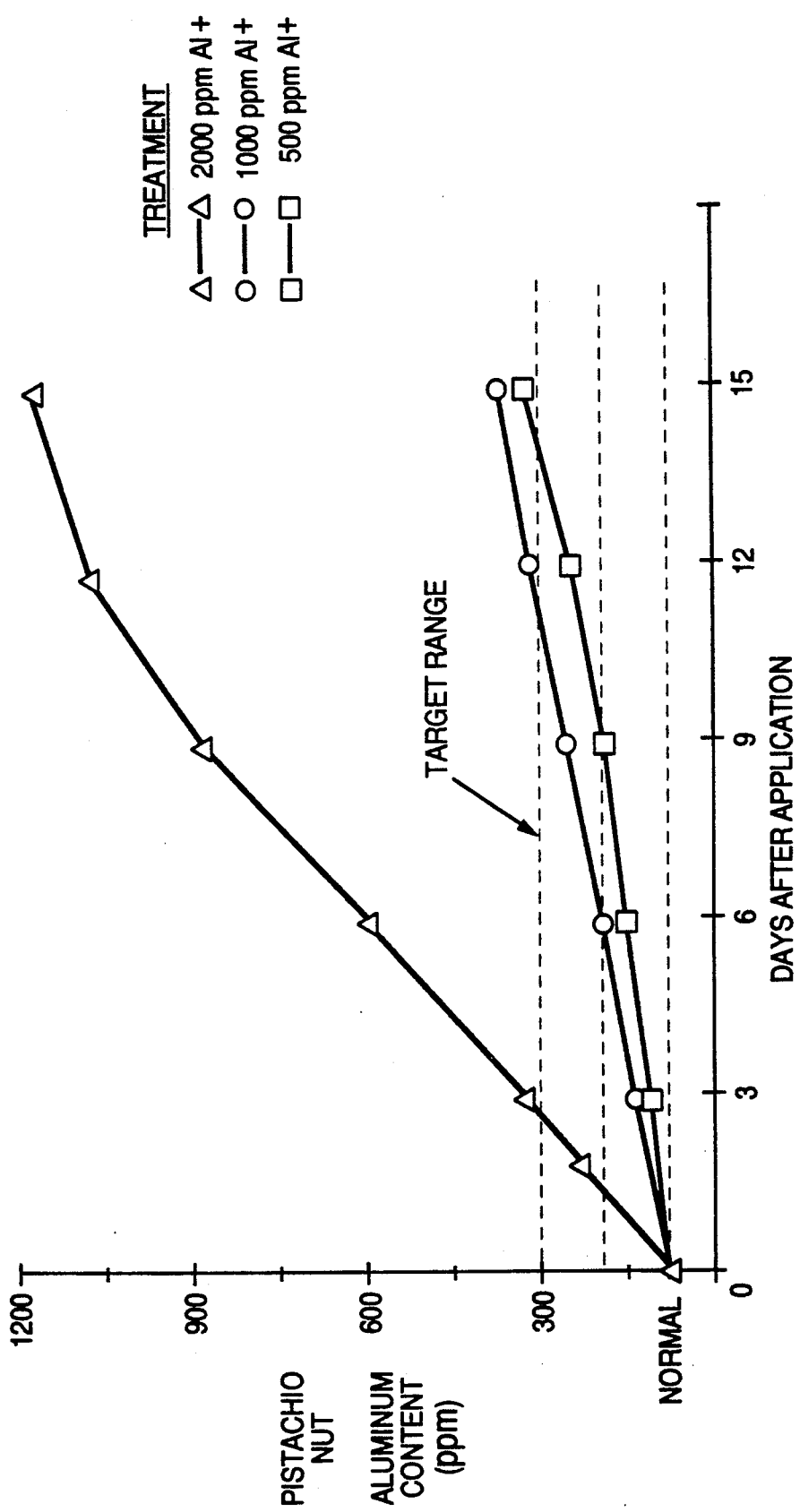
FIG. 3 is a graphic representation relating the aluminum content in the nut to the time since the application date of aluminum treatments in accordance with the invention applied to pistachio trees.

Numerous factors influence the effect of the present treatment, although not all are known or quantified. However, it is apparent that the application date prior to harvest (as shown in FIGS. 2 and 3), the selected wetting agent, the number of applications, the soil type and pH, cultural practices, irrigation scheme, time of year, type of root stock, fertilization levels and micronutrient status all exert some influence on the effect of the treatment applied to pistachio trees.

Although the effect of all factors is not known, reference to FIG. 4 will show empirically derived guidelines for applying the present treatment to pistachio trees, applicable to the normal harvest season in the Chowchilla and Madera, Calif. pistachio growing regions.

Figure 4A:
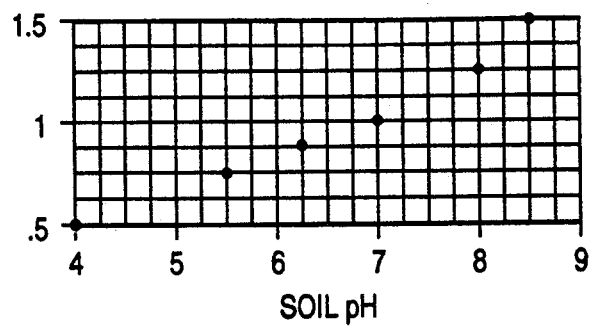
FIGS. 4A–C are graphic representations relating the dosage multiplier to soil pH, application date, and approximate $Al^+$ (PPM) levels determined in pistachio tree leaves at various dates for 96% aluminum sulfate treatments in accordance with the invention.
Figure 4B:
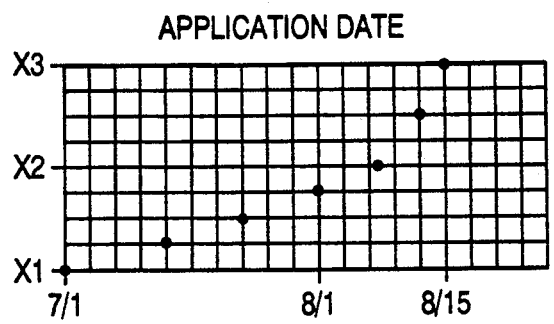
Figure 4C:
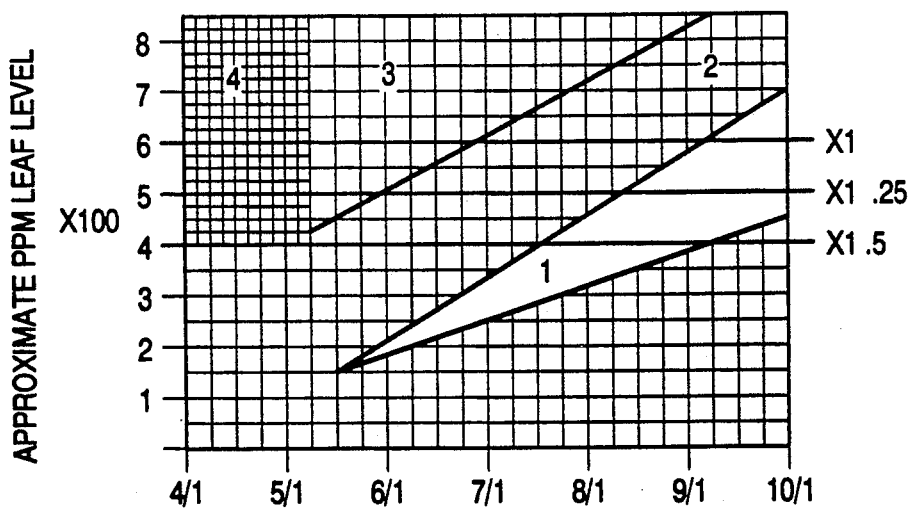

To determine the dose rate per tree for a single application, the amount of 96% aluminum sulfate to be applied begins with baseline levels as follows:
  8–12 year old tree use 1 oz/tree
  13–17 year old tree use 2 oz/tree
  18+ year old tree use 3 oz/tree Then, referring to FIG. 4A, the average soil pH will indicate a multiplier used to adjust the dosage amount. Similarly, from FIGS. 4B and 4C, the desired application date and the approximate Al+ (PPM) level measured in the tree leaf will likewise give similar multipliers. Calculation should provide a dose rate within the range of 2–2.5 oz to 6 oz/tree. Calculated values for dosage outside of these ranges will desirably be adjusted accordingly. It is presently considered undesirable to exceed a dose of 6 oz/tree, to avoid unnecessary damage.

EXAMPLE 5

In a manner similar to that described in Examples 1 and 2, the treatment of the present invention was applied to cotton plants in the following manner.

A plot of *Gossypium hirsutum* var. Acala SJ-2 cotton plants was examined and found that most had open bolls except for the plants growing on the outside borders of the plot. These plants were larger, greener and had mostly large, green closed bolls.

The bolls of a sample of these plants were sprayed to runoff with a spray consisting of 6 oz of 96% aluminum sulfate/gallon of water utilizing a 2 gallon Hudson sprayer. Control plants were sprayed with water only.

One week later, the plants were observed and the percentage of open versus closed bolls was compared. The results were as follows in Table VI.

TABLE VI

| | | Water (Control) | Aluminum Sulfate Spray |
|---|---|---|---|
| Total Plant Counted (Sprayed) | | 23 | 36 |
| Total Bolls Counted | | 405 | 377 |
| Average Number of Bolls/Plant | open | 9.6 | 6.3 |
| | closed | 8.0 | 4.1 |
| | total | 17.6 | 10.4 |
| Total Number of Bolls | open | 221 | 228 |
| | closed | 184 | 149 |
| Percent Bolls | open | 54.6 | 60.5 |

TABLE VI-continued

|  | Water (Control) | Aluminum Sulfate Spray |
|---|---|---|
| closed | 45.4 | 39.5 |
| Percent Reduction in Non-splits |  | 13.0% |

Thus it can be seen that similar results to those obtained with pistachio trees can be demonstrated in a distinct crop variety producing a different class of plant crop. Although the 13% reduction in non-splits is not as dramatic a result as those obtained for pistachio nuts, it should be emphasized that this test was performed without a wetting agent and the results obtained only seven days post treatment. In addition, further routine characterization of the treatment of the present invention applied to cotton bolls will optimize such applications and undoubtedly provide enhanced results.

Aluminum sulfate has been determined to be non-phytotoxic (Kinraide, T. B. and D. R. Parker, Physiol. Plant. 71:207-212 (1987)) and is generally recognized as safe and approved by the Food and Drug Administration as a miscellaneous and/or general purpose food additive (21 C.F.R. 182.1125). It is available as iron-free, food grade liquid alum or as a low-iron granular product (non-food grade) from General Chemical (Middletown, Ohio).

In addition, it is expected that split-shell edible crops treated in accordance with the present invention would not present any problem with increased aluminum levels in the portion consumed, as the above results demonstrate.

Therefore, it can be seen that the practice of this invention provides an increase in the proportion of split-shelled pistachio nuts in a crop without substantial risk of damage to the tree or the food crop.

Although the foregoing invention has been described in some detail, it will be understood that various modifications of the invention may be practiced while remaining with the scope of the appended claims.

I claim:

1. A method for treating crop plants which are a member of the genus Gossypium to increase the percentage of split-shell crops produced which comprises:
   exposing selected Gossypium, prior to crop harvest, to an aluminum treatment for times and under conditions sufficient to increase the proportion of split-shelled to non-split crops, relative to plants not so treated.

2. A method for treating crop plants which are a member of the group *Gossypium hirsutum, Gossypium arboreum, Gossypium herbaceum* or *Gossypium barbadense* to increase the percentage of split-shell crops produced which comprises:
   exposing selected *Gossypium hirsutum, Gossypium arboreum, Gossypium herbaceum* or *Gossypium barbadense*, prior to crop harvest, to an aluminum treatment for times and under conditions sufficient to increase the proportion of split-shelled to non-split crops, relative to plants not so treated.

* * * * *